US00PP33014P3

(12) United States Plant Patent
Brand et al.

(10) Patent No.: US PP33,014 P3
(45) Date of Patent: May 4, 2021

(54) SAND CHERRY PLANT NAMED 'UCONNPP002'

(50) Latin Name: *Prunus pumila*
Varietal Denomination: UCONNPP002

(71) Applicant: University of Connecticut, Farmington, CT (US)

(72) Inventors: Mark Henry Brand, Willington, CT (US); Bryan Allan Connolly, Mansfield Center, CT (US)

(73) Assignee: University of Connecticut, Farmington, CT (US)

( * ) Notice: Subject to any disclaimer, the term of this patent is extended or adjusted under 35 U.S.C. 154(b) by 0 days.

(21) Appl. No.: 16/501,934

(22) Filed: Jul. 8, 2019

(65) Prior Publication Data

US 2021/0015016 P1 Jan. 14, 2021

(51) Int. Cl.
*A01H 5/02* (2018.01)
*A01H 6/74* (2018.01)

(52) U.S. Cl.
USPC ..... Plt./182
CPC ..... *A01H 6/7445* (2018.05)

(58) Field of Classification Search
USPC ..... Plt./182, 181, 226
CPC ... A01H 5/02; A01H 5/00; A01H 5/08; A01H 6/74; A01H 6/7427; A01H 6/7472; A01H 6/7445
See application file for complete search history.

*Primary Examiner* — June Hwu
(74) *Attorney, Agent, or Firm* — Michael Best & Friedrich LLP

(57) ABSTRACT

This invention relates to an intermediate height Sand Cherry plant known as *Prunus pumila* and referred to by the name 'UCONNPP002', with a dense mounded form that is easy to produce and exhibits reliable landscape performance and ornamental traits as shown herein and described.

8 Drawing Sheets

STATEMENT REGARDING FEDERALLY SPONSORED RESEARCH

Figure 1:
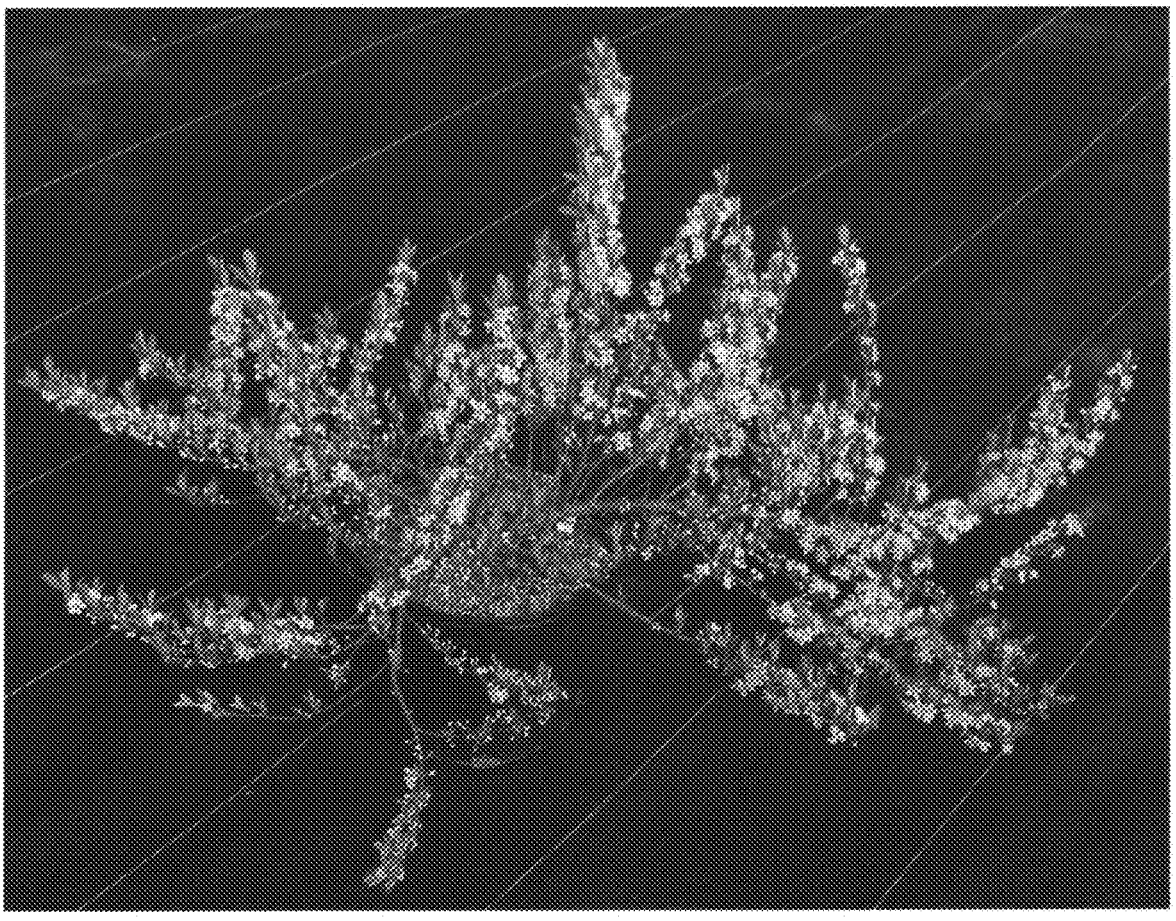

This invention was made with government support under grant 2015-31200-06009 awarded by USDA/National Institute of Food and Agriculture. The government has certain rights in the invention.

Latin name of the genus and species: *Prunus pumila.*
Variety denomination: 'UCONNPP002'.

BACKGROUND OF THE INVENTION

The present invention relates to a new and distinct cultivar of Sand Cherry plant, botanically known as *Prunus pumila* and hereinafter referred to by the name 'UCONNPP002'.

The new Sand Cherry plant is a product of a planned breeding program conducted by the Inventors in Storrs, Conn. The new Sand Cherry plant originated from a cross-pollination conducted by the Inventors during the Spring of 2010 of Sand Cherry *Prunus pumila* var. *depressa*; not patented, as the female, or seed parent and Sand Cherry *Prunus pumila* var. *susquehanae*; not patented, as the male, or pollen, parent. The new Sand Cherry plant was discovered and selected by the Inventors during the Spring of 2012 as a single plant from within the progeny of the stated cross-pollination in a controlled environment in Storrs, Conn.

Asexual reproduction of the new Sand Cherry plant by softwood stem cuttings in a controlled greenhouse environment in Storrs, Conn. since June 2012 has shown that the unique features of this new Sand Cherry plant are stable and reproduced true-to-type in successive generations of asexual reproduction.

SUMMARY OF THE INVENTION

Plants of the new Sand Cherry have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of the new Sand Cherry plant: Grows 50 to 60 cm tall with a 90 to 120 cm spread. Plants are densely branched with branching occurring low to the ground. The result is an intermediate spreading growth form that is full, dense, and rounded in outline. Flowering is profuse in April to early May, with the numerous small (2 cm diameter), single, 5-petaled, white, slightly fragrant flowers. Flowers attract pollinators. Fruits when present are deep black-purple and 0.75-1 cm in diameter. Spring and summer foliage are a deep lustrous green on the upper surface, with frosty green undersides. Leaves are typically between 7 and 8 cm long and 2.5-3.5 cm wide with acute bases and tips. Leaf margins are very finely serrated. Propagation is easy by rooting of firm softwood cuttings. Plants are easy to grow using standard container nursery production practices. Cold hardiness has not been fully evaluated, but the plant has proven to be fully hardy as far north as zone 3. Plants are well-adapted to a variety of challenging landscape uses. These characteristics in combination distinguish 'UCONNPP002' as a new and distinct Sand Cherry plant:

1. Intermediate spreading rounded or mounded habit;
2. Arching primary branching with upright secondary branches;
3. Mature size of 60 cm tall and 120 cm wide;
4. Heavy flowering (Meaning that flowers occur on nearly all branches, with flower clusters present at each node from the branch tip to close to the branch base. In bloom, branches appear as solid columns or wands of flowers);

5. Lustrous deep green summer foliage and brightly colored orange fall leaves; and
6. Easy propagation, culture, and rapid growth. Under container culture, annual shoot growth of 55 cm will be produced on primary shoots.

Plants of the new Sand Cherry can be compared to plants of *Prunus besseyi* 'P011S' Pawnee Buttes® Sand Cherry.

Plants of the new Sand Cherry differ primarily from plants of *Prunus besseyi* 'P011S' in their habit, flower size, rapid growth, and fall foliage display. *Prunus besseyi* 'P011S' grows to a mature height of 45 cm and 120 cm to 180 cm wide, while 'UCONNPP002' grows to 60 cm tall and 120 cm wide. Additionally, 'UCONNPP002' grows faster, has larger flowers, and brighter fall foliage than *Prunus besseyi* 'P011S'. 'UCONNPP002' has a mounded form, with a dense habit composed of overarching primary branches and upright secondary branches. Flowering is profuse in April into early May, with the production of numerous small (2 cm diameter), single, 5-petaled, white, fragrant flowers that attract pollinators. Fruits are 0.75-1 cm in diameter and dark purple to black. Spring and early summer foliage is deep shiny green above and grey green below. Propagation is easy by rooting of firm softwood cuttings. Plants are easy to grow in containers using standard container nursery production practices. Market-ready plants can be produced in 2 to 3 years. Cold hardiness has not been fully evaluated, but the plant should be fully hardy as far north as zone 3. Plants are landscape adaptable and will perform well in most landscape situations that have well-drained soil and light shade to full sun exposure.

BRIEF DESCRIPTION OF THE PHOTOGRAPHS

The accompanying colored photographs illustrate the overall appearance of the new Sand Cherry plant showing the colors as true as it is reasonably possible to obtain in colored reproductions of this type. Colors in the photographs may differ slightly from the color values cited in the detailed botanical description that accurately describe the colors of the new Sand Cherry plant.

The photograph in FIG. 1 is a side perspective view of a typical plant of 'UCONNPP002' grown in an outdoor nursery and in bloom in May. The plant shown is three years old.

Figure 2:
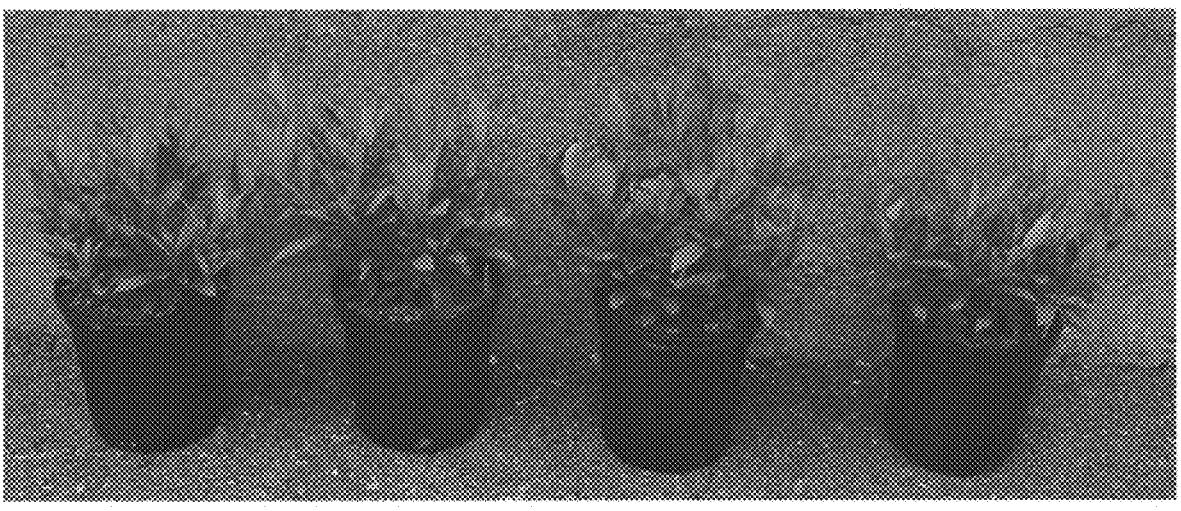

The photograph in FIG. 2 shows four typical second year container grown plants of 'UCONNPP002' produced from softwood cuttings.

Figure 3:
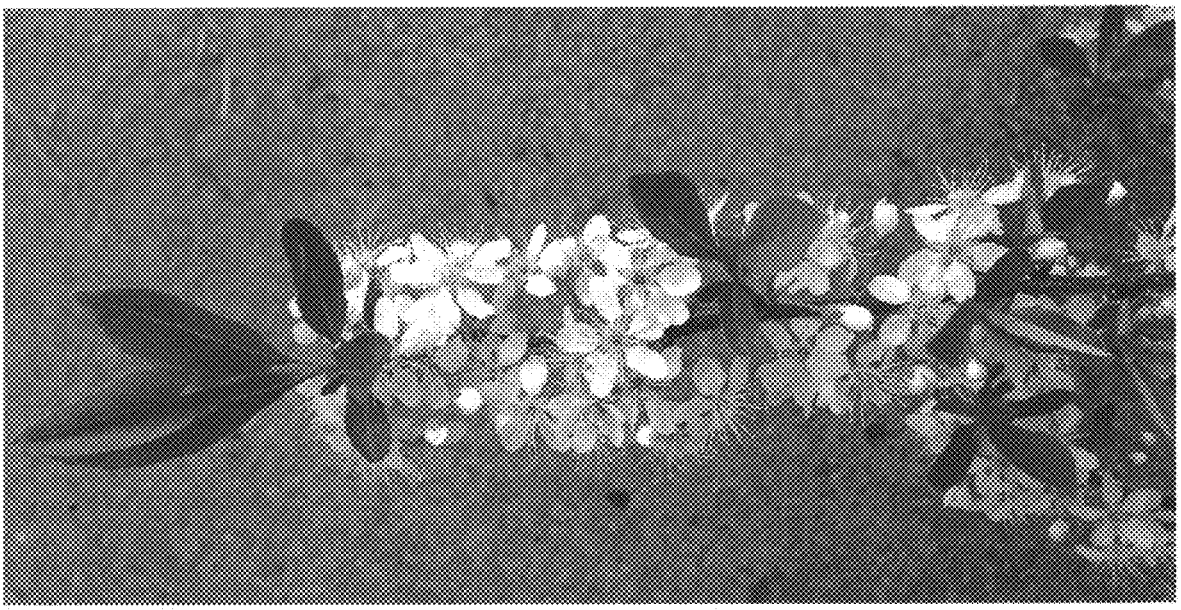

The photograph in FIG. 3 is a close up of the densely flowered branch of 'UCONNPP002' showing the abundant white 5-petaled flowers.

Figure 4:
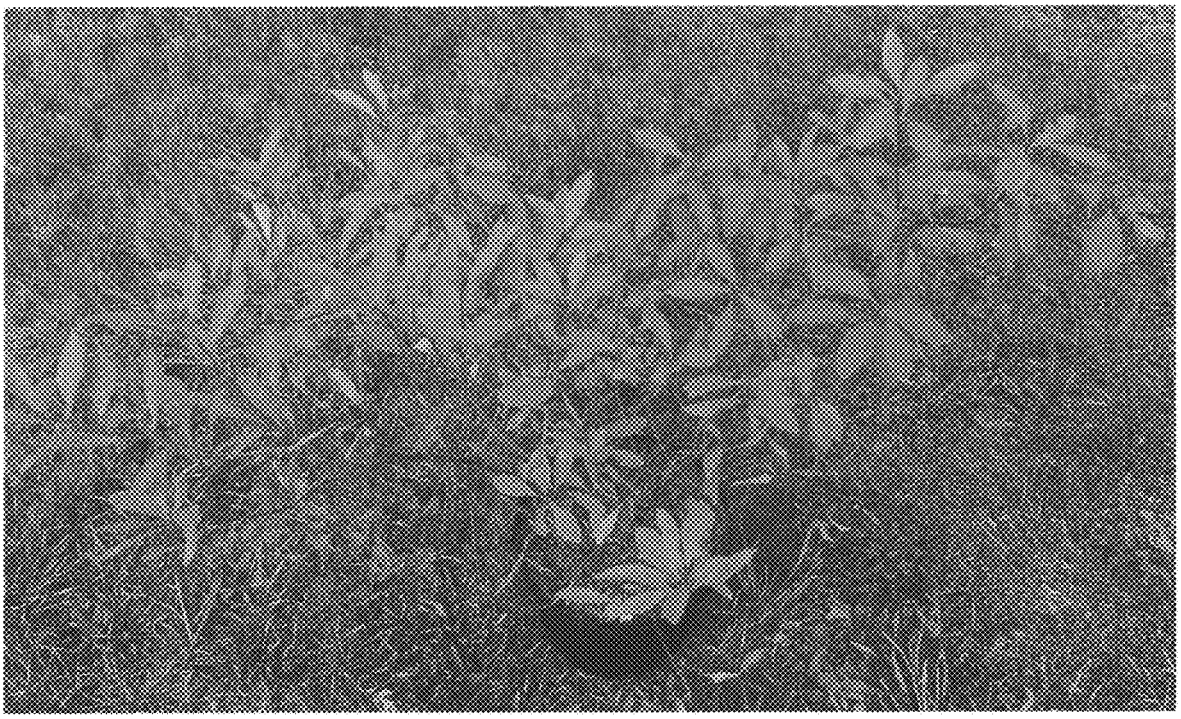

The photograph in FIG. 4 shows the brightly colored orange fall foliage of 'UCONNPP002'.

Figure 5:
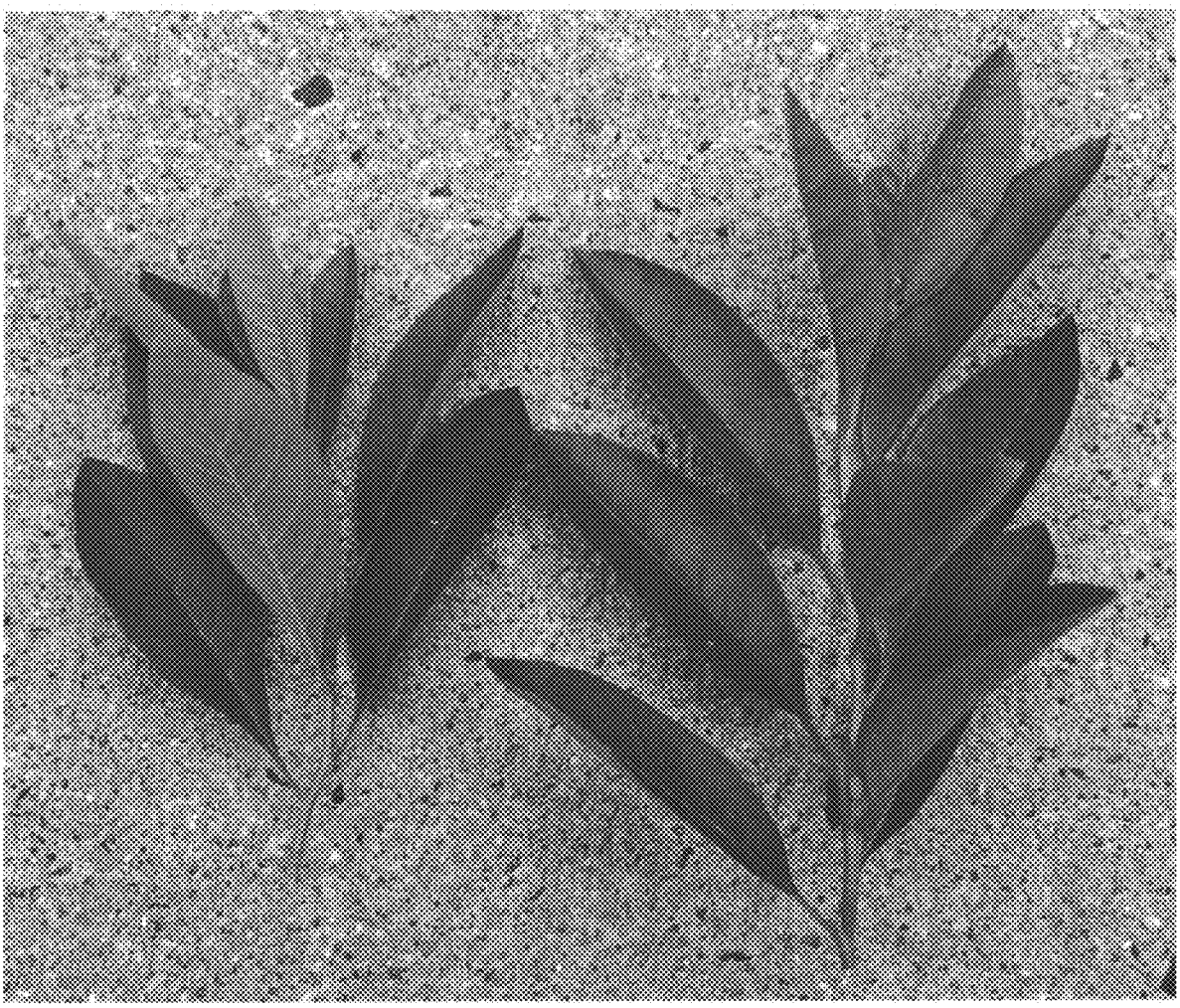

The photograph in FIG. 5 is a view of the early season shoot growth and foliage.

Figure 6:
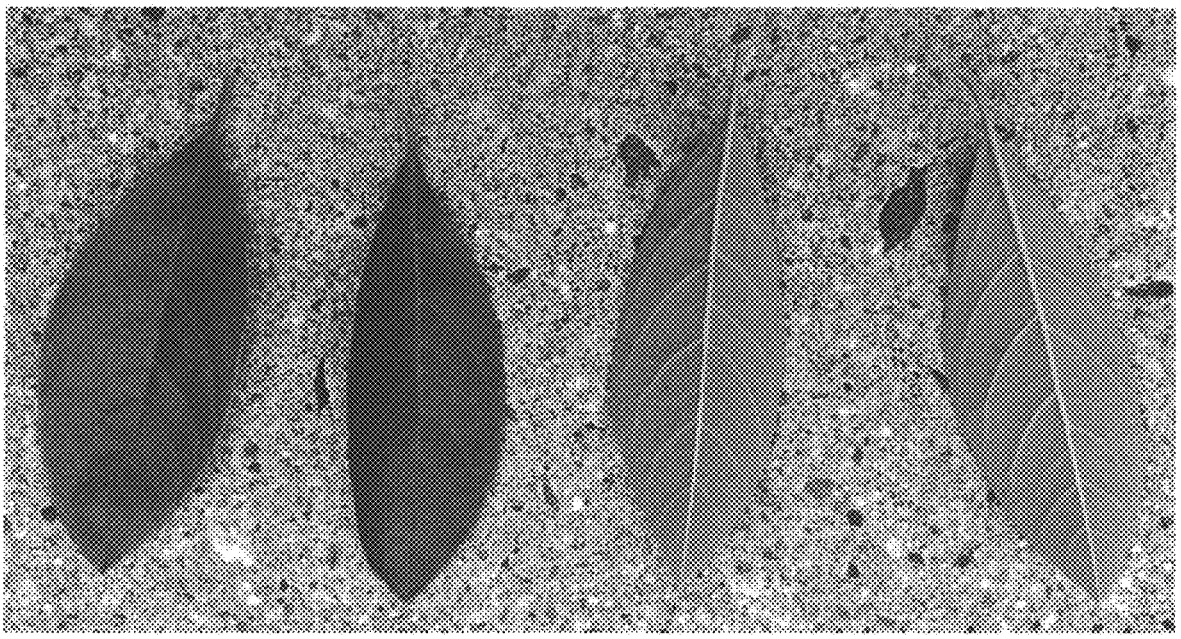

The photograph in FIG. 6 shows a close up of summer foliage exhibiting the deep green lustrous color on the leaves upper surface (adaxial surface, left two leaves) and the matte gray green of the undersides (abaxial surface, right two leaves).

Figure 7:
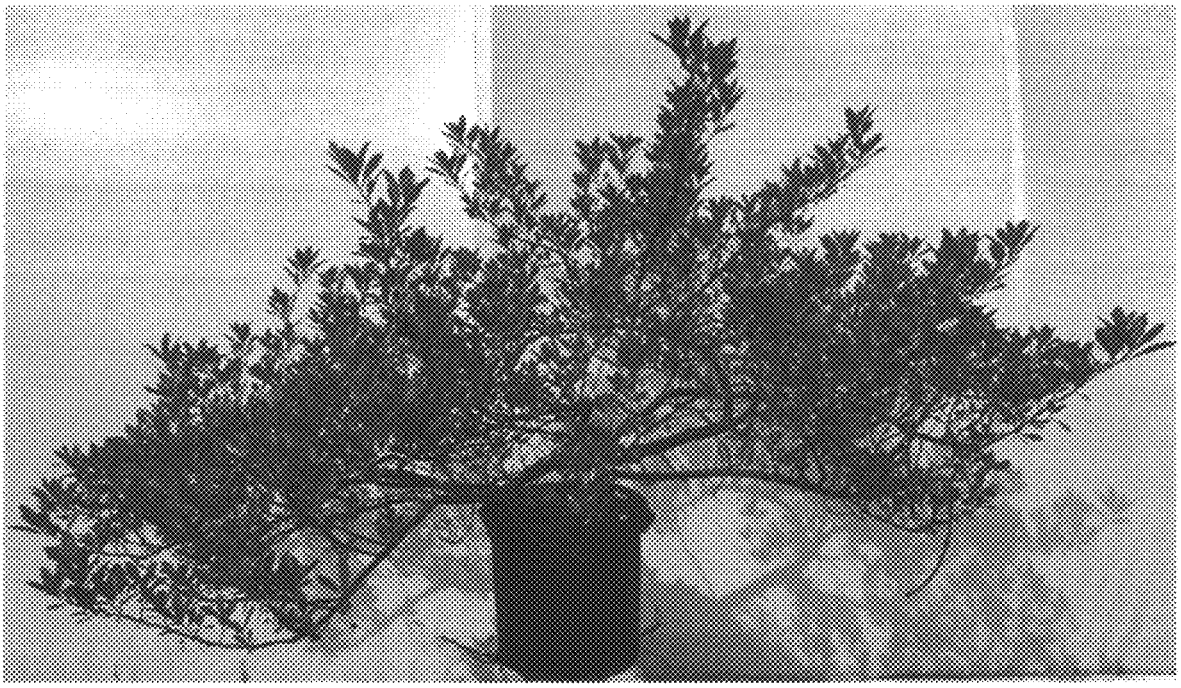

The photograph in FIG. 7 shows a side perspective view of a mature (3-years old), container-grown plant in foliage in late June.

Figure 8:
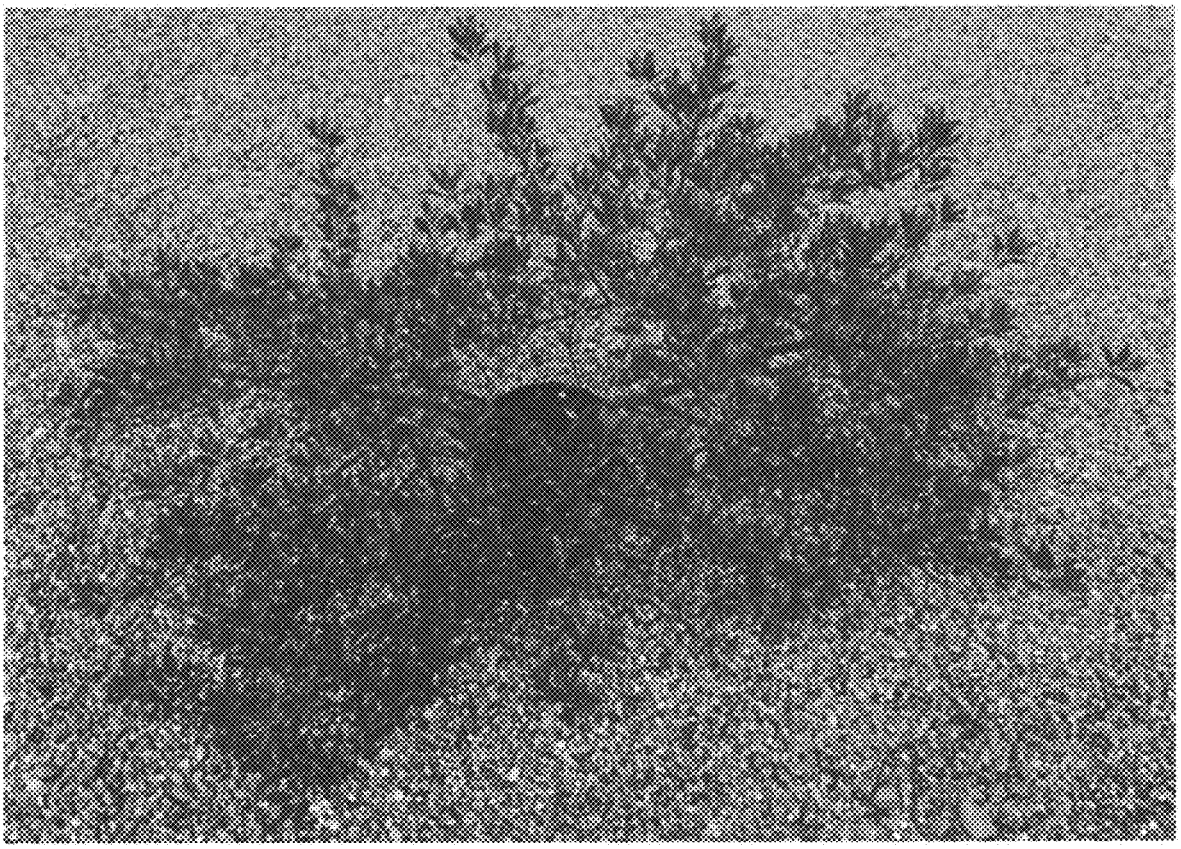

The photograph in FIG. 8 shows a top view of a mature (3-years old), container-grown plant in foliage in late June.

DETAILED BOTANICAL DESCRIPTION

The aforementioned photographs and following observations, measurements, and values describe plants grown during the spring in containers in an outdoor nursery in Storrs, Conn. and under cultural practices which closely approximate commercial Sand Cherry production. Plants used for the photographs and description were four years old. In the following detailed description, color references are made to The Royal Horticultural Society Colour Chart, 1995 Edition, except where general terms of ordinary dictionary significance are used.

Botanical classification: *Prunus pumila* 'UCONNPP002' (syn. *P. pumila* var. *depressa* x *P. pumila* var. *susquehanae*).

Parentage:

*Female, or seed, parent.*—*Prunus pumila* var. *depressa* (syn. *Prunus depressa*), not patented.

*Male, or pollen, parent.*—*Prunus pumila* var. *susquehanae* (syn. *Prunus susquehanae*), not patented.

Propagation:

*Type.*—Micropropagation using in vitro shoot multiplication followed by microshoot rooting. Murashige and Skoog medium containing 0.5 mg/L benzyladenine for shoot multiplication. Microshoots root easily in humidity chambers under non-sterile conditions with 1,000 ppm indole butyric acid in talc dip.

*Type.*—Softwood cuttings, but must be firm at the base. 1,000 to 3,000 ppm IBA in talc.

*Time to initiate roots* (*softwood cutting*), *summer.*—About 1 month at temperatures about 80-85° F. (~27-29° C.).

*Time to produce a rooted young plant, summer.*—About 1.5 months at temperatures about 80-85° F. (~27-29° C.).

*Root description.*—Fine, greenish-pink roots.

*Rooting habit.*—Fibrous and profuse.

Plant description:

*Plant form and growth habit.*—Mounded and dense, arching primary stem upright secondary branches.

*Plant height.*—About 60 cm.

*Plant diameter* (*area of spread*).—About 120 cm.

Lateral branch description:

*Length.*—About 10-50 cm.

*Diameter.*—About 2 mm to 3 mm.

*Internode length.*—About 1 cm.

*Aspect.*—90° angle from stem.

*Strength.*—Firm, but flexible.

*Texture.*—Smooth with 1 mm lenticels having a color close to 202C.

*Color.*—Close to 144B new growth and 166A mature bark.

*Thorns.*—Quantity: None.

Stipule description:

*Length.*—About 5.0 mm.

*Width.*—About 1.0 mm.

*Color.*—144B.

Leaf description:

*Arrangement.*—Alternate.

*Length.*—About 7.5 cm.

*Width.*—About 3.0 cm.

*Shape.*—Elliptical.

*Apex*.—Broadly acute.

*Base*.—Broadly acute.

*Margin*.—Very finely serrated.

*Texture, upper and lower surfaces*.—Slightly embossed veins, otherwise glabrous.

*Venation pattern*.—Pinnate.

*Color*.—Fully expanded mature leaves, upper surface: Close to 137A, 139A, 147A. Fully expanded mature leaves, lower surface: Close to 191A. Autumn foliage color is 43B, 44B, 44C on the adaxial surface.

*Petiole*.—Length: About 8 mm. Diameter: About 1-2 mm. Texture: glabrous. Color: 137C, 147B.

Flower description:

*Flower arrangement and habit*.—Numerous small flowers occur all along the length of the previous season's annual growth in umbel-like clusters; typically, about 65 flowers per 15 cm length of stem. Flowers occur at each node, numbering between 2-4 flowers per bud and 4-8 flowers per node from 2 flower buds.

*Fragrance*.—Significantly fragrant with a sweet, perfumed scent.

*Natural flowering season*.—Late April to early May in Connecticut.

*Flower longevity*.—10-14 days.

*Inflorescence length*.—About 2.5-3 cm.

*Inflorescence diameter*.—About 3 cm.

*Flower diameter*.—About 20 mm.

*Flower length* (*height*).—About 10 mm.

*Flower buds*.—Length: About 2-8 mm. Diameter: About 2-5 mm. Shape: Rounded. Color: Close to 155D.

*Petals*.—Arrangement: 5 petals in a single whorl. Petals may be separate, touching, or rarely overlapping slightly. Length: About 8-9 mm. Width: About 4-6 mm. Shape: Elliptical. Apex: Rounded. Margin: Entire, with slight irregular teeth. Texture, Upper and lower surfaces: smooth. Color: When opening, upper and lower surfaces: 155D. Fully opened, upper and lower surfaces: same as for opening.

*Sepals*.—Arrangement: 5 sepals in a single whorl. Length: About 2 mm. Width: About 1.5 mm. Shape: Broadly strap-like with rounded tip. Apex: Rounded. Base: Squared. Margin: Ciliate. Texture, upper and lower surfaces: smooth. Color: Upper and lower surfaces, 146C.

*Pedicels*.—Length: About 12-15 mm. Diameter: About 1 mm. Color: 145B. Aspect: About 30 to 60 degrees from stem axis.

*Reproductive organs*.—Stamens: Quantity: 27 to 31. Anther shape: Two kidney halves together make a round form. Anther length: About <1 mm. Anther color: Close to 12A. Pollen amount: Abundant. Pollen color: Close to 162A. Filament color: Close to 155D. Filament length: About 5 mm. Pistils: Quantity: 1 per flower. Pistil length: About 6-7 mm. Style length: About 4-5 mm. Style color: Close to 145A. Stigma color: Close to 145A. Ovary color: Close to 145A.

Seeds and fruits: Seed and fruit development have been observed on plants of the new Sand Cherry 'UCONNPP002'. Fruits: 0.75-1.0 cm diameter; rounded. Unripe fruit: 143C; ripe fruit 59B, 79A, 187A, 202A. Seeds: 0.5-0.75 cm diameter, rounded. Seed color: close to 162C, 163C.

Garden performance: Plants of the new Sand Cherry 'UCONNPP002' have been observed to have excellent garden performance in full sun and well-drained soils. They tolerate winter minimum temperatures down to about −30° F. (−34.4° C.) and are best adapted to locations receiving fewer than 50 summer days with temperatures exceeding 86° F. (30° C.).

Pathogen and pest resistance: Plants of the new Sand Cherry have been observed to be resistant to leaf spot. Plants of the new Sand Cherry have not been shown to be resistant to pests and other pathogens common to Sand Cherry plants.

It is claimed:

1. A new and distinct Sand Cherry plant named *Prunus pumila* 'UCONNPP002' as illustrated and described.

* * * * *